(12) United States Patent
Hwang et al.

(10) Patent No.: US 11,439,354 B2
(45) Date of Patent: Sep. 13, 2022

(54) SYSTEM AND METHOD FOR THREE-DIMENSIONALLY MAPPING HEART BY USING SENSING INFORMATION OF CATHETER

(71) Applicants: THE ASAN FOUNDATION, Seoul (KR); UNIVERSITY OF ULSAN FOUNDATION FOR INDUSTRY COOPERATION, Ulsan (KR)

(72) Inventors: Chang Mo Hwang, Seoul (KR); Young Hak Kim, Seoul (KR); Gi Byoung Nam, Seoul (KR); Jae Soon Choi, Seoul (KR); Gi Seok Jeong, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 648 days.

(21) Appl. No.: 16/483,039

(22) PCT Filed: Feb. 5, 2018

(86) PCT No.: PCT/KR2018/001513
§ 371 (c)(1),
(2) Date: Aug. 2, 2019

(87) PCT Pub. No.: WO2018/143747
PCT Pub. Date: Aug. 9, 2018

(65) Prior Publication Data
US 2020/0155073 A1   May 21, 2020

(30) Foreign Application Priority Data
Feb. 3, 2017 (KR) .................. 10-2017-0015790

(51) Int. Cl.
*A61B 5/00* (2006.01)
*A61B 5/287* (2021.01)
(Continued)

(52) U.S. Cl.
CPC ............ *A61B 5/6852* (2013.01); *A61B 5/287* (2021.01); *A61B 5/339* (2021.01); *A61B 34/20* (2016.02);
(Continued)

(58) Field of Classification Search
CPC ......... A61B 34/20; A61B 5/061; A61B 5/287; A61B 5/1076; A61B 5/6852; A61B 2034/2061
See application file for complete search history.

(56) References Cited

U.S. PATENT DOCUMENTS

| 7,781,724 B2 | 8/2010 | Childers et al. |
| 8,567,265 B2 | 10/2013 | Aeby et al. |

(Continued)

FOREIGN PATENT DOCUMENTS

| CN | 103536353 A | 1/2014 |
| CN | 104486991 A | 4/2015 |

(Continued)

OTHER PUBLICATIONS

"TactiCathTM Contact Force Ablation Catheter, Sensor EnabledTM", Instructions for Use, St. Jude Medical Inc., 2018, 29 pages.
(Continued)

*Primary Examiner* — Eun Hwa Kim
(74) *Attorney, Agent, or Firm* — Cantor Colburn LLP

(57) ABSTRACT

The present invention is a system for three-dimensionally mapping a heart, comprising: a mapping catheter including three or more optical cores each of which has a plurality of FBGs disposed in the lengthwise direction of a catheter body, and a plurality of electrodes disposed in the lengthwise (Continued)

direction of the catheter body and exposed on the outer circumferential surface of the catheter body, wherein the electrodes make contact with the inner wall of the heart; and a mapping processor for calculating coordinates of the FBGs by wavelength information of reflected light received from the three or more optical cores, and calculating coordinates of the electrodes from the coordinates of the FBGs so as to build a three-dimensional shape of the heart by using a sample point at which the plurality of electrodes make contact.

7 Claims, 13 Drawing Sheets

(51) Int. Cl.
    *A61M 25/01*     (2006.01)
    *A61B 34/20*     (2016.01)
    *A61B 5/339*     (2021.01)
    *A61B 18/14*     (2006.01)
    *A61B 18/00*     (2006.01)

(52) U.S. Cl.
CPC . *A61B 18/1492* (2013.01); *A61B 2018/00351* (2013.01); *A61B 2018/00577* (2013.01); *A61B 2018/00595* (2013.01); *A61B 2034/2061* (2016.02); *A61B 2562/0209* (2013.01); *A61M 25/0147* (2013.01)

(56) References Cited

U.S. PATENT DOCUMENTS

| | | | |
|---|---|---|---|
| 8,622,935 B1* | 1/2014 | Leo | A61B 5/0084 604/95.01 |
| 9,186,046 B2 | 11/2015 | Ramamurthy et al. | |
| 2003/0018251 A1 | 1/2003 | Solomon | |
| 2005/0187455 A1 | 8/2005 | Rashidi | |
| 2007/0156212 A1* | 7/2007 | Saxena | A61B 18/18 600/549 |
| 2010/0168620 A1 | 7/2010 | Klimovitch et al. | |
| 2011/0275951 A1 | 11/2011 | Lips et al. | |
| 2016/0296122 A1* | 10/2016 | Kim | A61B 5/0261 |
| 2019/0183373 A1 | 6/2019 | Kirschenman | |

FOREIGN PATENT DOCUMENTS

| | | |
|---|---|---|
| CN | 105073047 A | 11/2015 |
| JP | 2014161374 A | 9/2014 |
| JP | 2015505507 A | 2/2015 |
| JP | 2015066056 A | 4/2015 |
| JP | 2015519943 A | 7/2015 |
| JP | 6034028 B2 | 11/2016 |
| KR | 1020120072961 A | 7/2012 |
| KR | 101634334 B1 | 6/2016 |
| KR | 101760287 B1 | 7/2017 |
| WO | 2014028394 A1 | 2/2014 |
| WO | 2016070099 A1 | 5/2016 |

OTHER PUBLICATIONS

Lior Gepstein et al., "A Novel Method for Nonfluoroscopic Catheter-Based Electroanatomical Mapping of the Heart," Circulation, 1997, vol. 95, No. 6.

International Search Report dated May 3, 2018 for PCT/KR2018/001513.

Jong-Il Choi et al., "NavX™ cardiac mapping system," International Journal of Arrhythmia, 2013, pp. 8-13, vol. 14, No. 1, English abstract.

Tina Lin et al., "ThermoCool® SmartTouch® Catheter—The Evidence So Far for Contact Force Technology and the Role of VisiTag™ Module," Arrhythmia & Electrophysiology Review, 2014, pp. 44-47.

* cited by examiner

SYSTEM AND METHOD FOR THREE-DIMENSIONALLY MAPPING HEART BY USING SENSING INFORMATION OF CATHETER

TECHNICAL FIELD

Example embodiments relate to a three-dimensional (3D) heart mapping system and method using sensing information of a catheter, and more particularly, to a mapping system and method that may shape a heart by calculating a location of an electrode to be in contact with an inner wall of the heart based on shape information of a mapping catheter including a fiber Bragg grating (FBG) optical fiber.

BACKGROUND ART

In general, a catheter is a medical instrument used by inserting a tube into a body of a patient to apply a radiofrequency treatment to an affected area or part of the body of the patient, or injecting a medical substance or ingredient into the body and externally discharging a body fluid from the body.

However, when performing a medical procedure using the catheter, there may be some cases that a tip of the catheter, which is at a front end of the catheter, does damage to an affected body part of a patient due to an excessive pressure applied by the tip to the affected body part of the patient. In contrast, when the front end of the catheter comes into contact with the affected body part at an extremely low pressure, the affected body part may not be completely or desirably treated. Thus, a pressure to be applied by the catheter to the affected body part may need to be precisely measured based on a location at which the medical procedure is performed and on a type of the medical procedure.

In addition, the catheter may be used for an interventional procedure performed using imaging equipment to treat a target affected body part of a patient by the catheter being guided to the target affected body part. The interventional procedure is a minimally invasive medical procedure, and is thus highly reliable in terms of safety and prognosis. In addition, it may minimize pains and scars, and thus patients may be highly satisfied with such procedure. Thus, the interventional procedure is being used in a greater range of medical and technical applications. However, the interventional procedure requires a precise manipulation of a medical practitioner, and a success or failure in the interventional procedure depends on experience and ability of the medical practitioner. In addition, when a precise location adjustment is not performed while treating a sensitive part such as, for example, a cardiovascular system, based on a type of medical procedure or surgery, blood vessels may be damaged, causing other complications and radiation exposure. Thus, it is essential to develop medical apparatuses and equipment that enable such procedure to be precisely and accurately performed within a short period of time. Thus, constructing a control system configured to remotely perform the interventional procedure has emerged as one of main technological issues. This control system may need to minimize complications that may be caused due to a lack of experiences and abilities of medical practitioners, for patients, and to prevent continuous exposure to radiation by operating on many patients, for medical practitioners.

To construct such a remote control system for a cardiovascular interventional procedure, the remote control system may include, in terms of hardware, a catheter to be guided to a heart for the procedure, a haptic master manipulator with which a medical practitioner operates or manipulates the catheter, and a slave robot configured to control the catheter while interworking with the manipulation of a master. Here, the catheter may include an electrode for transferring a stent or performing a radio frequency ablation, and may thus perform a radio frequency catheter ablation. As described above, the catheter may need to be precisely controlled. Here, for remote control, a degree of functional precision, for example, sensing information, location information, and electrocardiogram (ECG) information of the catheter, may affect, directly or indirectly, the success or failure of the procedure.

For the cardiovascular interventional procedure, the catheter may enter the interior of a heart to be in contact with an inner wall of the heart, and then map the heart. For the cardiovascular interventional procedure, it is essential to precisely measure a magnitude and a direction of a contact force or a pressure applied to a front end of the catheter. For the radio frequency catheter ablation in particular, when a radio frequency (RF) is applied with the catheter not being in contact with a target tissue, blood present around an electrode of the catheter located inside an atrium of the heart may be coagulated and a blood clot may be formed to result in a cerebral infarction and an embolus in vital organs. In contrast, when the catheter is in an excessively close contact with the inner wall of the heart that is continuously contracted and dilated, a severer medical accident such as perforation of the inner wall of the heart may happen.

Thus, it is required to precisely measure a pressure applied to the front end of the catheter during mapping or an RF ablation of a body tissue for the interventional procedure, and accordingly various types of sensors have been proposed to measure a pressure applied to a tip of the catheter. Conventionally, a force sensor using an electric pressure-sensitive device of which current to be output varies based on an external force applied from an outside may be used. However, using the force sensor using the electric pressure-sensitive device, a change in current to be output may not be great when a fine external force is applied, and a high-priced device or equipment may be needed to precisely measure such a change in current. In addition, when increasing an amount of current by increasing a size of the electric pressure-sensitive device, a size of the catheter may also increase.

As one of solutions to such an issue of precisely measuring a pressure to be applied to a tip of a catheter, U.S. Pat. No. 8,567,265 discloses a triaxial fiber force sensing catheter configured to sense a force at a front end in triaxial directions using an optical fiber. FIG. 1 illustrates a pressure sensing catheter disclosed in U.S. Pat. No. 8,567,265. Referring to FIG. 1, the catheter disclosed in U.S. Pat. No. 8,567,265 may calculate a curve value and a contact pressure through a Fabry-Perot interferometer based analysis of a reflection of light generated when a front end of the catheter is curved or bent using an optical fiber, dissimilar to existing electric pressure-sensitive types. The catheter disclosed in U.S. Pat. No. 8,567,265 includes a structural member 102 in which triple gaps 921 are formed in a sensing assembly 92. In the structural member 102, the slit-shaped gaps 921 on which a part of an outer circumferential surface is disposed at 120°, respectively, are formed in different heights. Here, three optical fibers 104 are disposed and then fixed thereto such that output ends of optical cores are respectively located at the gaps 921 at an interval of 120°. The triple gaps 921 forms a segment structure such as a spring. When an external force F is applied in a certain direction to the front end, the interval of the gaps 921 at respective locations may change. Thus, a magnitude and a direction of a contact force may be sensed through an analysis of multiple interference of light reflected and received by the optical fibers 104.

FIG. 2 illustrates a sensing principle of a catheter to which the catheter-related technology disclosed in U.S. Pat. No. 8,567,265 of FIG. 1 is applied. This sensing principle is an excerpt from the description of a TactiCath™ product of St. Jude Medical Inc. In general, a Fabry-Perot interference may be embodied by inserting a single gap cavity in between two mirrors having a high reflectivity. A fundamental principle of the Fabry-Perot interference may be to select only desired data by generating multiple interference in the gap cavity when multiple wavelengths, for example, $\lambda 1$, $\lambda 2$, $\lambda 3$, ..., that are transferred through an optical fiber are incident on a filter, and then transmitting only a certain wavelength and reflecting other wavelengths. Referring to FIG. 2, the gaps 921 of the structural member 102 are illustrated as a Fabry-Perot cavity, and a magnitude and a direction of an external force may be calculated using optical wavelength information of wavelengths interfered through the three gaps 921 based on the Fabry-Perot interference.

Another product to which such front end pressure-sensitive catheter technology proposed as illustrated in FIGS. 1 and 2 is applied includes, for example, a ThermoCool SmartTouch catheter introduced by Biosense Webster of Johnson & Johnson Medical. The ThermoCool SmartTouch catheter may accurately transfer information associated with a direction of the catheter and strength of a force in a contact portion, and have an increased level of safety, and it is thus approved by US Food and Drug Administration (FDA) and launched in Korea.

As described above, the technology for measuring a pressure to be applied to a tip of a catheter has been contributed to the development of a catheter to which an optical fiber with a high level of safety is applied, in terms of using an electric pressure-sensitive device.

However, the existing catheter described with reference to FIGS. 1 and 2 requires the structural member 102, in addition to an optical fiber, for the sensing assembly 92. The slit-shaped gaps 921 of the structural member 102 may need to be formed to be opened at an interval of 120° and have different heights. The slit-shaped gaps 921 of the structural member 102 at equidistant intervals may need to be formed in a lengthwise direction. Thus, a length of the structural member 102 may occupy a relatively great portion of a front end of the existing catheter, and there may thus be a limitation in measuring a precise displacement of the front end of the catheter. In addition, analyzing optical wavelength information through a multiple Fabry-Perot interference may make designing a system more complicated and increase a unit cost for production.

In addition to mapping of a heart, location information of the catheter that is currently in the mapped heart may need to be accurately verified for the cardiovascular interventional procedure. In related arts, an electroanatomical mapping (EAM) method may be used to obtain, in real time, a location of the catheter in the heart. The EAM method may use a non-contact mapping system, and three-dimensionally construct a location of the catheter through a body surface patch inducing a transthoracic electrical field using a multielectrode array.

FIG. 3 illustrates a principle of an Ensite NavX™ product of St. Jude Medical Inc. to which an EAM method is applied. This principle is an excerpt from the description in a dimensional mapping system-related document published in International Journal of Arrhythmia Referring to FIG. 3. the Ensite NavX™ product may be an impedance-based mapping system that has a total of six electrode patches with three pairs of the patches each pair being attached to front and back portions, left and right portions, and upper and lower portions, respectively, of a body surface of a patient, and forms a transthoracic electrical field when a current signal of approximately 8 kilohertz (KHz) is output from the six electrodes, and also forms a voltage gradient through a tissue in the heart along each axis, and then measures such voltage at an electrode of the catheter, and thus verifies a location of the catheter.

However, the impedance-based heart mapping method described in the non-patent document may have an intrinsic issue of decreasing accuracy of a three-dimensional (3D) image due to a deformation of an electrical field that may be caused by a technical problem. Thus, to reduce such an error, experience of an operator or a medical practitioner is considered an important factor in a registration process.

In addition, a system for detecting a location of the catheter using a magnetic field has been proposed as another mapping method different from the EAM method described above with reference to FIG. 3. FIGS. 4 and 5 illustrate a principle of a CARTO product of Biosense Webster to which such magnetic field mapping method is applied. This principle is an excerpt from the relevant description and drawings of a document entitled "A Novel Method for Nonfluoroscopic Catheter-Based Electroanatomical Mapping of the Heart." Referring to FIG. 4, the CARTO product of Biosense Webster includes a ring electrode at a tip of a mapping catheter, and a location sensor provided inside the catheter by being accepted therein. Referring to FIG. 5, a location pad includes three coils C1, C2, and C3 each being configured to form a magnetic field, and the location sensor embedded in the catheter is configured to measure strength of a magnetic field of the location pad and calculate a distance to map a location of the catheter.

According to the non-patent document, the system to which the location sensing using a magnetic field is applied may be more advantageous in terms of costs, compared to a fluoroscopic catheter system. However, a system that may obtain refined mapping in real time has not been optimized yet. In addition, when a catheter bends, rapidly detecting such bending has remained as a technical issue to be solved. Thus, the system is applied in combination with a conventional mapping catheter.

Thus, the EAM method may have its limitation in terms of anatomical accuracy because it performs 3D mapping based on a transthoracic electrical field, and a reference source shakes and the electrical field changes due to a movement of a heart and a respiration of a patient during an actual procedure. In addition, the mapping catheter may perform only sequential mapping based on a contact, instead of simultaneous multiple mapping, by a plurality of electrodes, and thus activation mapping may not be available for arrhythmia with an irregular pulse such as, for example, atrial fibrillation. In addition, the mapping method using a magnetic field may not readily obtain, in real time, information associated with a deformation, for example, bending of a catheter, and optimizing the system has still remained as a technical issue to be solved. Thus, there is a desire for another mapping method that may improve accuracy in mapping a shape of a heart and sensing a location of a catheter.

Therefore, according to example embodiments, there is provided a mapping system and method with reference to U.S. Pat. No. 7,781,724. The mapping system and method may map a shape of a heart only using information of a mapping catheter itself without an electrical field or a magnetic field by detecting, in real time, a shape of a catheter itself without formation of an electrical field or magnetic field, obtaining a coordinate value of the detected shape, and verifying a location of the catheter. Thus, the mapping system and method may map the shape of the heart using location information of the verified location of the catheter.

U.S. Pat. No. 7,781,724 discloses technology for constructing a real-time shape that is bent in addition to a location of an optical fiber, using three fiber Bragg grating (FBG) optical fibers. FIG. 6 illustrates a fiber optic position and shape sensing device 10 disclosed in U.S. Pat. No. 7,781,724 (hereinafter "the related art"). Referring to FIG. 6, the fiber optic position and shape sensing device 10 includes an optical fiber 20 including three or more fiber cores 30, 35, and 40, an array of FBGs 50 disposed within each of the fiber cores 30, 35, and 40, a reflectometer 70, and a coupling device 25 configured to couple multiple optical fibers 55, 57, and 59. The FBGs 50 may be a type of optical sensor, and configured to reflect a wavelength of light that changes in response to a change in temperature or strain. Each of the FBGs 50 may be manufactured with an intrinsic Bragg wavelength, and disposed in a lengthwise direction of a fiber core to reflect an intrinsic wavelength of light and change an optical wavelength at a corresponding location, and thus detect a change in strain to be applied to the optical fiber.

According to the related art of FIG. 6, a frequency displacement may be detected from each of the FBGs 50 disposed on a same cross section of the three optical cores 30, 35, and 40 arranged at 120°. A two-dimensional (2D) shape deformation of the optical fibers 55, 57, and 59 may be obtained through a calculation of frequency displacements measured from two optical cores. The related art discloses that a 3D shape deformation of the optical fibers 55, 57, and 59 may be obtained by a calculation of frequency displacements measured from three optical cores.

According to the example embodiments described herein, the mapping system and method is provided based on an idea that a 3D shape of an optical fiber may be measured using at least three FBG optical cores, and that an accurate location of a catheter may be detected based on coordinate values of FBGs obtained by sensing a shape of the catheter. Thus, the mapping system and method is provided herein with reference to the related art by designing a mapping catheter suitable for the cardiovascular interventional procedure due to simultaneous detection of a shape of the catheter and a pressure at a front end thereof, and the mapping system and method may thus map a shape of a heart using measurement information of the mapping catheter.

DISCLOSURE OF INVENTION

Technical Goals

An aspect provides a mapping system and method that may construct a three-dimensional (3D) shape of a heart using a mapping catheter configured to detect a 3D shape of a catheter in real time and measure a direction and a magnitude of an external force applied to a front end of the catheter. The mapping system and method may construct the 3D shape of the heart based on sensing information of the mapping catheter.

Technical Solutions

According to an example embodiment, there is provided a three-dimensional (3D) heart mapping system, including a mapping catheter including at least three optical cores each having a plurality of fiber Bragg gratings (FBGs) disposed in a lengthwise direction of a catheter body, and a plurality of electrodes disposed in the lengthwise direction of the catheter body and exposed on an outer circumferential surface of the catheter body, in which the electrodes come into contact with an inner wall of a heart, and including a mapping processor configured to calculate coordinates of the FBGs based on optical wavelength information of reflected light received from the at least three optical cores and calculate coordinates of the electrodes from the coordinates of the FBGs so as to construct a 3D shape of the heart by using sample points with which the electrodes are in contact.

The mapping catheter may include the catheter body having a first area defined by a path formed with at least one channel, and a second area defined by a front end provided with a tip to be condensed as an external force is applied. The FBGs may sense a shape of the catheter body based on optical wavelength information of a group of FBGs disposed in the first area, and sense the external force applied to the tip based on optical wavelength information of a group of FBGs disposed in the second area.

The mapping catheter may form a loop at the front end, when the electrodes are connected to respective driving wires and the catheter body is bent at points at which the electrodes are located by the driving wires being pulled in or pulled out. The mapping processor may calculate coordinates of FBGs corresponding to locations of the electrodes at which a pressure is sensed when the loop comes into contact with the inner wall of the heart, and obtain the sample points in a linear form.

The mapping catheter may be steered to scan the inner wall of the heart by the loop.

The mapping processor may include a control module configured to set a path of the mapping catheter to remotely control the mapping catheter. The control module may measure a pressure to be applied to a tip of the mapping catheter using optical wavelength information by the FBGs, and set a branch point entering the heart based on a pattern of change in external force generated when the tip is not in contact with blood vessels.

According to another example embodiment, there is provided a 3D heart mapping method including a step (a) of measuring a physiological response from an electrode exposed on a surface of a mapping catheter including an optical fiber having a plurality of FBGs, a step (b) of calculating coordinates of the FBGs located on a same cross section as the electrode from which the physiological response is measured in the step (a), a step (c) of calculating a coordinate of the electrode from which the physiological response is measured, from the coordinates of the FBGs calculated in the step (b), and a step (d) of constructing a 3D shape of a heart by sampling the coordinate of the electrode calculated in the step (c).

Advantageous Effects

According to example embodiments described herein, there is provided a mapping system. When a curved or bent front end of a mapping catheter forms a loop and the loop comes into contact with an inner wall of a heart, the mapping system may calculate a coordinate of the loop based on optical wavelength information of a fiber Bragg grating (FBG) optical fiber at such a contact point and obtain sample points in a linear form, thereby constructing a three-dimensional (3D) shape of the heart by a scanning operation of the loop.

According to the example embodiments, there is no need to use an additional electrode patch to construct the shape of the heart. In addition, it is possible to construct the shape of the heart only using information of the mapping catheter entering the heart, and thus construct an accurate 3D shape of the heart without being affected by a fine movement by, for example, respiration of a patient.

BEST MODE FOR CARRYING OUT THE INVENTION

Figure 1:
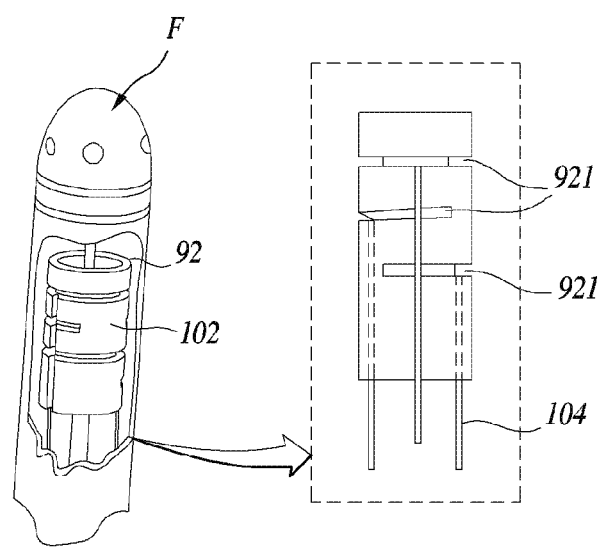
FIG. 1 illustrates a pressure sensing catheter using an optical fiber according to a related art.
Figure 2:
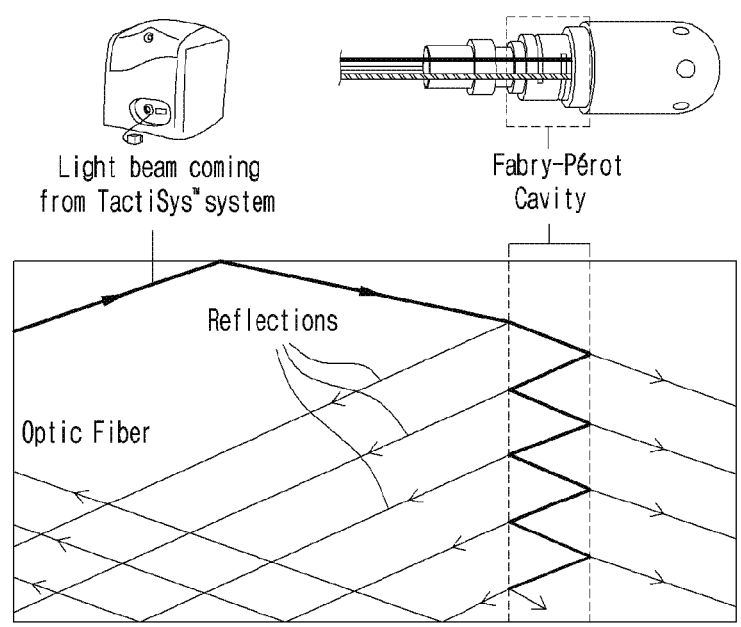
FIG. 2 illustrates a sensing principle of a pressure sensing catheter product to which technology described with reference to FIG. 1 is applied.
Figure 3:
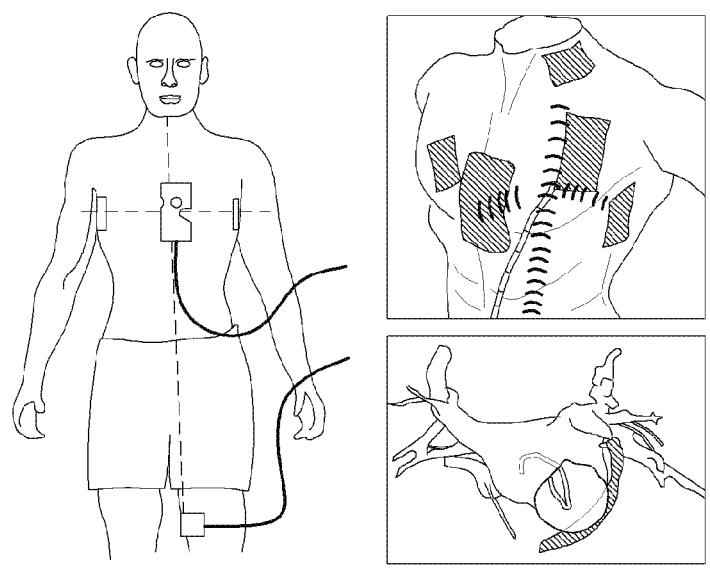
FIG. 3 illustrates a catheter system to which an electroanatomical mapping method is applied according to a related art.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings.

The technical goals and advantageous effects are not limited to what has been described in the foregoing, and other effects may be explicitly understood by those skilled in the art from the following description. Also, in the description of example embodiments, detailed description of well-known related structures or functions will be omitted when it is deemed that such description will cause ambiguous interpretation of the present disclosure.

Figure 7:
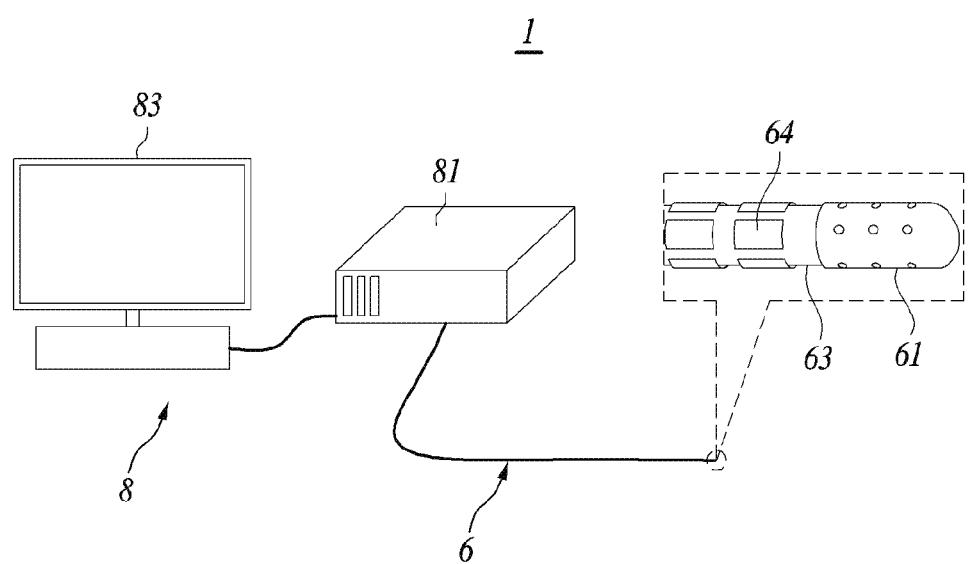
FIG. 7 illustrates a three-dimensional (3D) heart mapping system according to an example embodiment.

FIG. 7 illustrates a three-dimensional (3D) heart mapping system 1 according to an example embodiment. Referring to FIG. 7, the 3D heart mapping system 1 includes a mapping catheter 6 and an optical wavelength analyzer 8. The 3D heart mapping system 1 may construct a shape of a heart using sensing information of the mapping catheter 6. The mapping catheter 6 may be configured to measure an external force to be applied to a tip 61 and a bent shape of the mapping catheter 6. In detail, the mapping catheter 6 may measure a magnitude and a direction of the external force to be applied to the tip 61, and obtain 3D pressure information of the tip 61 being in contact with an inner wall of the heart.

In addition, an optical fiber 65 of the mapping catheter 6 may be embodied as a sensing assembly configured to sense a shape of a catheter body 63 while measuring a pressure of the tip 61.

The sensing assembly embodied by the optical fiber 65 may sense the shape of the catheter body 63 by determining a degree of refraction at which the catheter body 63 is bent and a direction of the refraction, in addition to the magnitude and the direction of the external force to be applied to the tip 61. Here, to measure the pressure of the tip 61 and sense the shape of the mapping catheter 6, optical wavelength information of light wavelengths by fiber Bragg gratings (PBGs) 6511 and 6513 provided in the optical fiber 65 may be calculated. The optical wavelength information may be classified into wavelength information for a group of the FBGs 6511 to sense the shape of the catheter body 63, and wavelength information for a group of the FBGs 6513 to measure the pressure of the tip 61. How the measurement is performed will be described hereinafter with reference to FIGS. 9 through 11.

The 3D heart mapping system 1 includes, in addition to the mapping catheter 6, the optical wavelength analyzer 8 including a mapping processor 81 configured to calculate a plurality of sets of optical wavelength information received from the optical fiber 65, and calculate the magnitude and the direction of the external force to be applied to the tip 61 and calculate the shape of the catheter body 63, and a display 83 configured to visually display a result of the calculating. Hereinafter, the mapping catheter 6 will be described in detail.

The mapping catheter 6 includes three or more optical cores in which the PBGs 6511 and 6513 are arranged along a lengthwise direction of the catheter body 63, and a plurality of electrodes 64 arranged along the lengthwise direction of the catheter body 63 and exposed on an outer circumferential surface of the catheter body 63. The electrodes 64 may come into contact with an inner wall of a heart.

The mapping catheter 6 also includes an elastic member 67, in addition to the catheter body 63, the electrodes 64, the optical fiber 65, and the tip 61.

In an example, the tip 61 is connected to an electrode wire 33 to electrically communicate therewith, and heated by electric power applied from an outside to remove a myocardial tissue. In another example, the tip 61 may also be embodied as an electrical sensor device configured to measure a biosignal such as an electrocardiogram (ECG) signal. The tip 61 is coupled to a front end of the catheter body 63. The tip 61 is connected to at least one driving wire 615 such that the mapping catheter 6 is steered as a direction of the front end is controlled by the driving wire 615 being pulled in or out. An outer surface of the tip 61 is provided with a water supply hole 613 configured to discharge cooling water to be transferred to an irrigation tube 31.

Referring to FIG. 7, the mapping catheter 6 is provided with the electrodes 64 exposed on the surface of the catheter body 63, in addition to an electrode provided at the tip 61. The electrodes 64 provided on the surface of the catheter body 63 may be provided as an ablation electrode to cauterize a myocardial tissue being in contact or as a sensor to measure a biosignal. Although not illustrated, each of the electrodes 64 is connected to the driving wire 615 and the electrode wire 33, and an area of the catheter body 63 on which each of the electrodes 64 is located may be bent. Thus, the catheter body 63 may form a loop 7 at the front end. The loop 7 formed by the catheter body 63, in lieu of the tip 61, may come into contact with a target point, and thus the electrodes 64 may cauterize a large area, or a large area of the electrodes 64 may make contact with an inner wall of a heart and perform a scanning operation to obtain shape information of the heart within a relatively short period of time.

Figure 8:
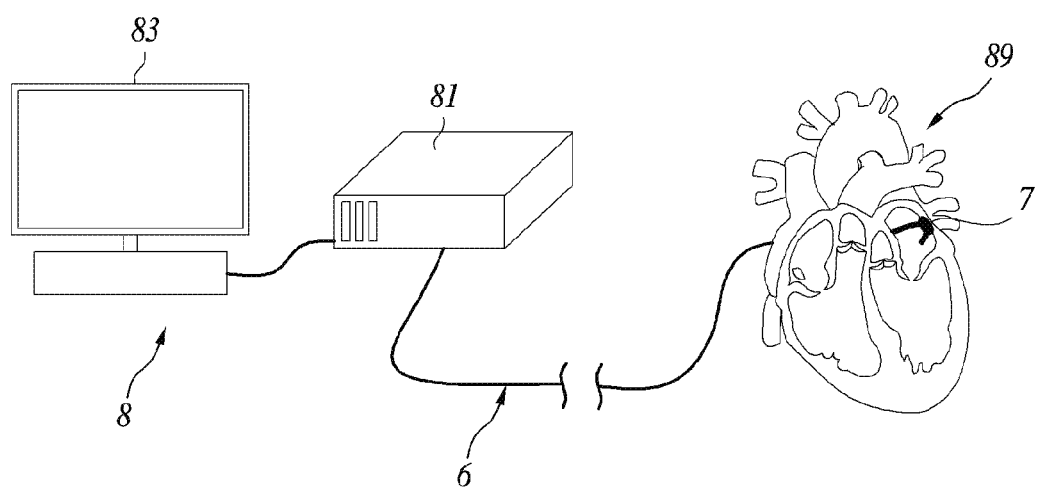
FIG. 8 illustrates an entry of a mapping catheter of the mapping system of FIG. 7 into a heart.

FIG. 8 illustrates an entry of a mapping catheter of a mapping system of FIG. 7 into a heart. The electrodes 64 may be provided in a form of segments, for example, four to six electrode segments being provided on a circumferential surface of the catheter body 63. Referring to FIG. 8, for ablation or heart mapping, one circumferential surface of the loop 7 of the catheter body 63 may come into contact with an inner wall of a heart 9. For the ablation, a catheter including the electrodes 64 provided along the circumferential surface of the catheter body 63 may generate a blood clot on another surface not being in contact with the inner wall of the heart 9 when a high frequency is applied, and may cause a serious side effect. Thus, it is desirable that the electrodes 64 are provided in the catheter body 63 in a form of segments as illustrated in FIG. 7, and thus a high frequency may be applied only to a segment of the electrodes 64 at a point in contact.

The catheter body 63 enters the heart 9 and guides, to a target point, a treatment element including an electrode that needs to be inserted to remove a myocardial tissue. In general, a heated electrode may come into contact with a myocardial tissue and remove the myocardial tissue, for the treatment of tachyarrhythmia such as paroxysmal supraventricular tachycardia, atrial tachycardia, and paroxysmal ventricular tachycardia. Here, the electrode being at a temperature of approximately 50° C. to 60° C. may perform ablation for approximately 60 seconds. A catheter configured to treat arrhythmia when an electrode of the catheter reaches a portion or a point in which such arrhythmia occurs and then removes a myocardial tissue there may be classified as an ablation catheter. An electrode may also be provided to measure a biosignal, in addition to such purpose of removing a myocardial tissue, and a treatment element such as a stent may be guided based on a purpose of treatment and a surgical method. The catheter body 63 may be formed of a flexible material having a high level of biocompatibility to allow an electrode at a front end or other treatment elements used for an ablation catheter or a mapping catheter to enter a target portion.

Figure 9:
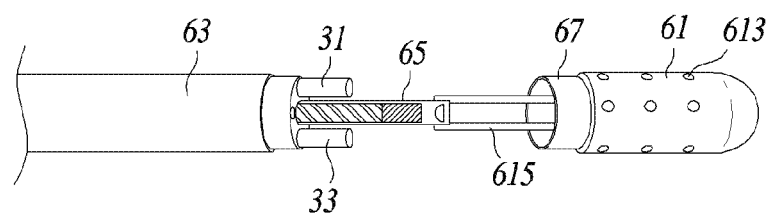
FIG. 9 illustrates an exploded view of a front end of a mapping catheter according to an example embodiment.
Figure 10:
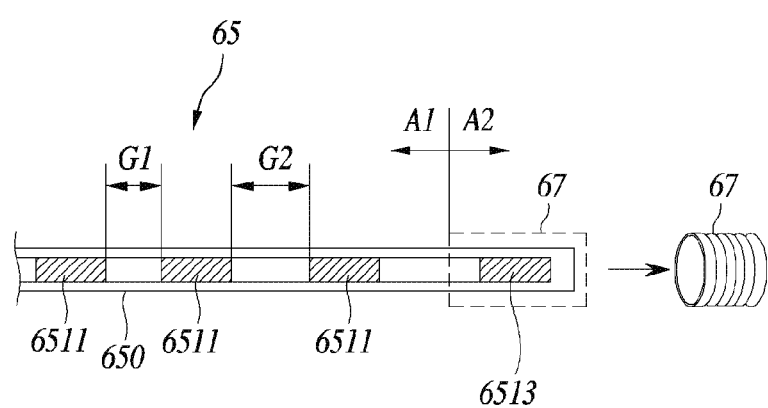
FIG. 10 illustrates an internal view of an optical fiber of a mapping catheter according to an example embodiment.

FIG. 9 illustrates an exploded view of a front end of the mapping catheter 6 according to an example embodiment. FIG. 10 illustrates an internal view of an optical fiber of a catheter according to an example embodiment.

Referring to FIGS. 9 and 10, the catheter body 63 includes a first area A1 defined by a path in which at least one channel is formed, and a second area A2 defined by the front end provided with the tip 61 to which an external force is to be applied. Such definition is to explicitly describe structural characteristics and functions. That is, the path from the front end of the mapping catheter 6 to before the tip 61 and the elastic member 67 is classified as the first area A1, and a path of the front end after the path of the first area A1 is classified as the second area A2 to detect a pressure of the tip 61.

Figure 4:
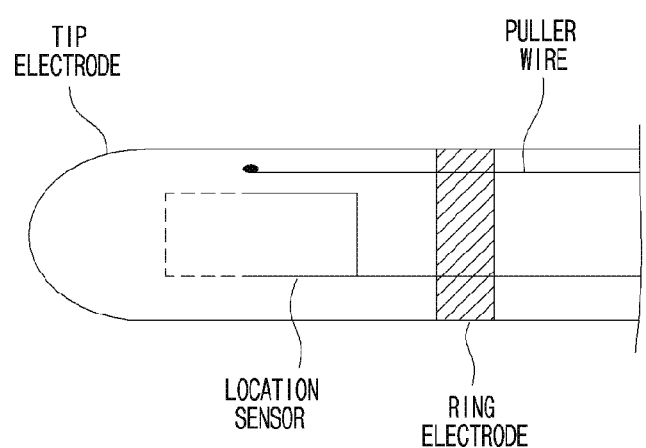
FIGS. 4 and 5 illustrate a catheter system to which a magnetic field mapping method is applied according to a related art.
Figure 5:
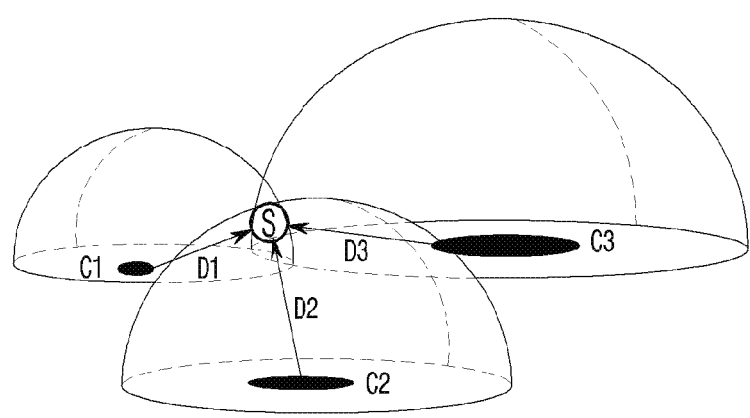
Figure 6:
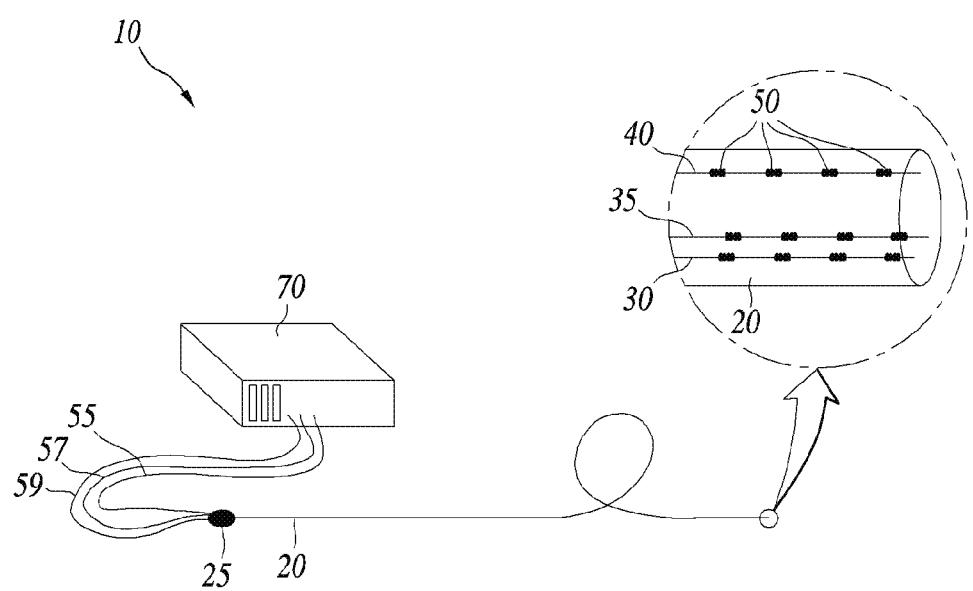
FIG. 6 illustrates a shape of an optical fiber and a location detecting system according to a related art.

Here, at least one channel may be formed in the catheter body 63. Referring back to FIGS. 4 and 5, an example of the channel formed in the catheter body 63 is illustrated. The channel may include a channel into which the optical fiber 65 penetrates to measure a pressure, a channel into which the irrigation tube 31 penetrates to cool a heated electrode, a channel into which the electrode wire 33 penetrates to provide power to the electrode, and a channel into which the driving wire 615 penetrates to steer the mapping catheter 6.

The optical fiber 65 penetrates in a channel, and the FBGs 6511 and 6513 are arranged along the lengthwise direction of the catheter body 63. The optical fiber 65 is provided such that optical cores 651 are shielded in a sheath 650, and a clad layer is formed such that light is transferred through the optical cores 651 through total reflection of light in the sheath 650.

The optical fiber 65 includes the plurality of optical cores 651, and the optical cores 651 will be described hereinafter with reference to FIG. 11. In the optical cores 651, the FBGs 6511 and 6513, which are optical grating sensors, are arranged in the lengthwise direction. An FBG is a generally known optical sensor device, and configured to reflect a wavelength of light that varies in response to a temperature or a deformation of a strain. An FBG may be constructed by exposing a photosensitive fiber of a short length to a periodic distribution of light intensity using a holographic interference or a phase mask. When light of a broad wavelength band is transmitted to an FBG, a reflection from each portion that replaces a refractive index may be structurally disturbed or interfered only at a certain optical wavelength which is a Bragg wavelength. Thus, the FBG may induce an effective reflection of a certain optical frequency, and cause a wavelength transition or change in received optical information. In the FBG, a Bragg wavelength functions as a grating interval, and the FBG is thus prepared with various Bragg wavelengths. The FBG having the various Bragg wavelengths may reflect an intrinsic wavelength of light in each wavelength band.

According to an example embodiment, the FBGs 6511 and 6513 arranged in the lengthwise direction of the optical cores 651 may sense a strain deformation occurring when a certain point of the optical cores 651 is bent. However, when the FBGs 6511 and 6513 are disposed on the optical cores 651 at equidistant intervals, a portion of optical transition wavelength information to be received may be lost due to an interference by the FBGs 6511 and 6513 even though light having broadband wavelengths enters. In detail, a portion of light incident on the optical cores 651 may come into contact with a first FBG, which is first located, to be reflected, and a remaining portion of the light may pass through the first FBG to proceed forward. Similarly, a portion of the light passing through the first FBG may come into contact with a second FBG to be reflected, and the reflected light may come into contact again with the first FBG A portion of the reflected light may pass through the first FBG and be combined with the light initially reflected by the first FBG, and a remaining portion of the light may be reflected again by the first FBG to proceed towards the second FBG This may occur repeatedly in gratings located subsequent to the second FBG Thus, light entering the optical cores 651 may be repeatedly reflected and transmitted (or passed through) by the plurality of FBGs 6511 and 6513 to cause an interference therewith. Thus, although light of broadband wavelengths enters, most of transition wavelength information may be lost due to multiple interference, and thus sensitivity may be insufficient to distinguish a physical change such as, for example, bending of the optical cores 651 in each segment.

Thus, according to an example embodiment, the FBGs 6511 and 6513 may be disposed on the optical cores 65 at different intervals, and the intervals may increase in a direction towards the front end. Referring to FIG. 9, a first interval in a direction of proximal portion is indicated as G1, and a second interval of the front end in a direction of remote portion is indicated as G2. The intervals between the FBGs arranged in a direction of front end such that G2 is greater than G1 may increase gradually.

Such an arrangement may allow polarized reflected light to have different wavelength differences when light experiencing interference by a plurality of gratings comes out again through a light entrance. In detail, the polarized reflected light may be reflected light that is polarized in an x-axial direction which is a lengthwise direction and in a y-axial direction in a vertical direction, respectively, and the reflected light may have different wavelength bands and the reflected light have wavelengths independently by the plurality of gratings. Thus, since intervals among the gratings are different, a change in wavelength to be detected may facilitate the detection of a state of refraction.

Further, the FBGs 6511 and 6513 may sense a shape of the catheter body 63 by optical wavelength information of the group of FBGs 6511 arranged in the first area A1, and sense an external force to be applied to the tip 61 by optical wavelength information of the group of FBGs 6513 arranged in the second area A2.

The optical wavelength analyzer 8 may process light information by separately processing a transition wavelength band of the first group of FBGs 6511 arranged in the first area A1 and a transition wavelength band of the second group of FBGs 6513 arranged in the second area A2. Here, a plurality of grating sensors in the first group of FBGs 6511 may be used to calculate a bent curve and a direction at corresponding locations, and a grating sensor in the second group of FBGs 6513 may be used to calculate a contact force by the tip 61 being pressurized or bent.

The elastic member 67 is provided to surround the optical fiber 65 on an inner side of the front end, and is formed with a material having an elastic force different from that of the catheter body 63 so as to concentrate an external force to be applied to the tip 61 onto the front end.

The elastic member 67 is provided in the second area A2, and the group of FBGs 6513 arranged in the second area A2 is located inside the elastic member 67.

Although it is desirable to form an integral type of the mapping catheter 6 with a single material in order not to have bumps, it may also be required to provide, at the front end, a material having an elastic force different from that of the catheter body 63 in order to accurately measure a magnitude and a direction of an external force to be applied to the tip 61. According to an example embodiment, it is possible to obtain a significant measurement value when a physical change by a pressure applied to the tip 61 is concentrated on the second group of FBGs 6513 arranged in the second area A2. When the catheter body 63 formed of a same elastic material surrounds the second area A2, a magnitude of an external force may be transferred to the catheter body 63, although the external force in a direction of linear axis is applied to the tip 61 at the front end, and thus it may be applied along with the physical change of the first area A1 in which the first group of FBGs 6511 is located. Thus, it may not be possible to measure an accurate contact force of the tip 61. In addition, although an external force in an outer side direction is applied to the tip 61 at the front end, a physical change is not concentrated on the second area A2 in which the second group of FBGs 6513 is located. Thus, it may not be easy to accurately measure an amount of change in amount of light. Due to such reasons, it may be desirable to assemble the elastic member 67 at the front end of the catheter body 63 along with the tip 61 and provide the elastic member 67 formed with a different material that covers a gap G disposed on an inner side of the catheter body 63. The elastic member 67 may be formed with a material that is more flexible than that of the catheter body 63, and a material, for example, a spring, may be used.

Figure 11:
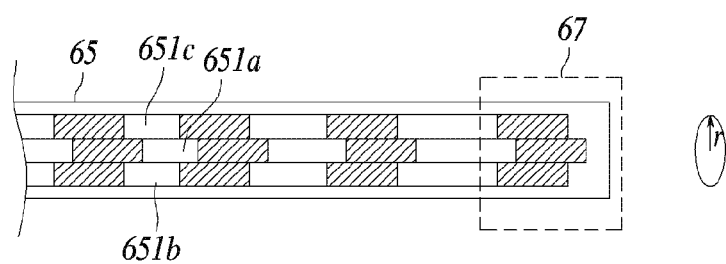
FIG. 11 illustrates an internal view of an optical fiber of a mapping catheter according to another example embodiment.

FIG. 11 illustrates an internal view of the optical fiber 65 including multiple optical cores 651a, 651b, and 651c according to another example embodiment.

Referring to FIG. 11, the optical fiber 65 includes three or more optical cores 651a, 651b, and 651c, and the optical cores 651a, 651b, and 651c are disposed within a predetermined radius from a linear axis of the catheter body 63. Although the multiple optical cores 651a, 651b, and 651c are illustrated as being included in the single optical fiber 65, three or more optical cores 65 each having a single optical core 651 may also be provided in the catheter body 63.

For example, when at least three optical cores 651 are arranged on a cross section of the optical fiber 65 at intervals of 120°, how much the optical core 651 is bent and a direction of such bending may be calculated through a triplet operation of optical wavelength information received from the at least three optical cores 651. In this example, when the at least three optical cores 651 each having a plurality of optical gratings are provided, it is possible to calculate a 3D deformation of the catheter body 63. For an example of a sensing principle of using the three optical cores 651, reference may be made to U.S. Pat. No. 7,781,724. Referring to paragraphs [0046] to [0071], and FIGS. 6 through 9 of U.S. Pat. No. 7,781,724, there is provided a method of calculating a bend radius r, and a bend direction and a bend angle a with respect to the bend radius r, in addition to an x' axis which is a center distance from a curve center to a core boundary, using three strain values from three FBG optical cores disposed on a same cross section. On the same principle, at least three different sets of FBG sensing information with different radii from the curve center may be used as transition wavelength information or changed wavelength information to calculate a strain variable and calculate a curved shape of the catheter body 63.

In addition, on the same principle, the three or more optical cores 651a, 651b, and 651c may sense a direction and a magnitude of an external force to be applied to the tip 61 based on optical wavelength information associated with at least three wavelengths that are changed or experience transition after having been past through the second group of FBGs 6513 arranged in the second area A2.

According to an example embodiment, the optical fiber 65 may penetrate in a channel corresponding to the linear axis of the catheter body 63. That is, the optical fiber 65 may be disposed at a center of the catheter body 63.

The optical cores 651 may be less flexible than the catheter body 63 due to a characteristic of a material used. Thus, when the optical cores 651 are disposed on an outer side relative to the linear axis of the catheter body 63, a bend range of the mapping catheter 6 to be bent or curved by the driving wire 615 may be restricted. For the same reason, as illustrated in FIG. 9, it is desirable to design the optical fiber 65 to be disposed at a central channel corresponding to the linear axis of the catheter body 63, and the irrigation tube 31 or the electrode wire 33 to be disposed at a channel located in an outer side direction of the linear axis. Such design may be a contrast to an example design disclosed in U.S. Pat. No. 8,567,265 by which a plurality of optical cores needs to be arranged on an outer side of a catheter body. Thus, based on an operable range of an optical fiber that is less flexible, a structural design that may improve a bend range of a catheter may be used to improve a bend range of the catheter.

Referring back to FIG. 11, when light of different wavelength bands passes through the first group of FBGs 6511 arranged in the first area A, and sets of changed wavelength information associated with the changed wavelengths are distinguished from one another by the three or more optical cores 651a, 651b, and 651c, a shape of the catheter body 63 may be sensed by calculating a bend direction and a bend angle of the optical fiber 65 based on the distinguished three or more sets of optical wavelength information.

The three or more optical cores 651a, 651b, and 651c may distinguish respective reflected light and obtain the distinguished reflected light. Thus, on the three or more optical cores 651a, 651b, and 651c, light of different wavelength bands may be incident. For example, light of red (R), green (G), and blue (B) wavelengths may be incident on the three or more optical cores 651a, 651b, and 651c, respectively. In addition, the three or more optical cores 651a, 651b, and 651c may determine a shape deformation occurring in the first group of FBGs 6511 by comparing an amount of light of the R wavelength, an amount of light of the G wavelength, and B wavelength transition information.

According to another example embodiment, on the three or more optical cores 651a, 651b, and 651c, light of broadband wavelengths may be incident with time differences, respectively. Here, when sets of light information are distinguished from one another based on a time difference with which light of a same wavelength band passes through the first group of FBGs 6511 arranged in the first area A1, the three or more optical cores 651a, 651b, and 651c may sense a shape of the catheter body 63 by calculating a bend direction and a bend angle of the optical fiber 65 based on the distinguished three or more sets of optical wavelength information.

The optical wavelength analyzer 8 includes the mapping processor 81 and the display 83.

The optical wavelength analyzer 8 may calculate a shape of the catheter body 63 based on the optical wavelength information of the first group of FBGs 6511 arranged in the first area A1 among the plurality of FBGs, and calculate an external force to be applied to the tip 61 based on the optical wavelength information of the second group of FBGs 6513 arranged in the second area A2. The optical wavelength analyzer 8 may include an optical source configured to allow light to transmit or enter for each wavelength band or with a time difference in order to distinguish sets of wavelength information of the multiple optical cores 651a, 651b, and 651c.

The mapping processor 81 may calculate received three sets of light information, and the display 83 may visually display the calculated shape of the catheter body 63, and the calculated pressure and direction of the tip 61. When the front end of the catheter body 63 forms the loop 7, the mapping processor 81 may detect whether the loop 7 is in contact with an inner wall of a heart, being in contact to be suitable for a curve of the inner wall, based on a change in wavelengths of FBGs located on the loop 7.

Subsequently, the mapping processor 81 may calculate coordinates of the FBGs disposed on the loop 7 based on wavelength information of reflected light received from the three or more optical cores 65, calculate coordinates of the electrodes 64 from the coordinates of the FBGs, and construct a 3D shape of the heart 9 using sample points with which the electrodes 64 are in contact.

According to another example embodiment, the mapping processor 81 may include a control module configured to set a path of the mapping catheter 6 and remotely control the mapping catheter 6 based on the set path. The control module may measure a pressure that acts on the tip 61 of the mapping catheter 6 using optical wavelength information by the FBGs, and set a branch point entering the heart based on a pattern of change in external force generated when the tip 61 is not in contact with a blood vessel.

Figure 12:
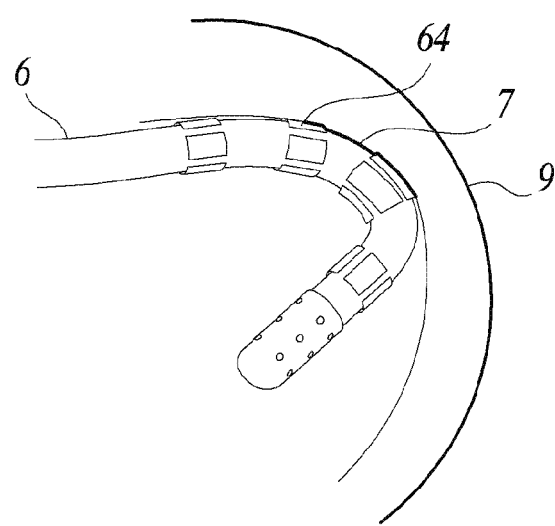
FIGS. 12 and 13 illustrate a scanning operation of a mapping catheter according to an example embodiment.
Figure 13:
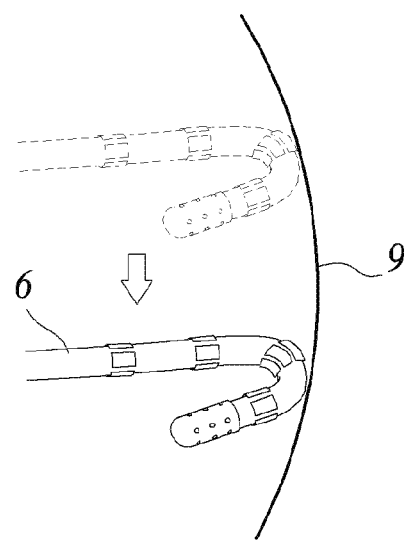

FIGS. 12 and 13 illustrate a scanning operation of the mapping catheter 6 according to an example embodiment. Referring to FIG. 12, the mapping catheter 6 enters the heart 9, and the front end thereof bends by an operation of the driving wire 615 connected to each of the electrodes 64. In response to the front end being bent, the loop 7 of the mapping catheter 6, in lieu of the tip 61, comes into contact with the inner wall of the heart 9. Due to a change in physical property of the catheter body 63 in response to the contact, wavelength change or transition information of FBGs disposed in the loop 7 is obtained by the mapping processor 81. Referring to FIG. 13, subsequently, the mapping catheter 6 is steered to scan the inner wall of the heart 9 by the loop 7.

The mapping processor 81 obtains, as a line, sample points of the inner wall of the heart 9 being in contact, by calculating a location of the electrodes 64 on a surface of the loop 7 from the FBG coordinate value of the loop 7 from which a pressure is sensed. Here, line information about such line may be used to complete surface information of the inner wall of the heart 9 as the mapping catheter 6 performs a scanning operation, and to construct a final 3D shape of the heart 9 when the scanning operation is completed at all the points of the inner all of the heart 9.

According to another example embodiment, a 3D heart mapping method to be performed using the mapping catheter system 1 described herein may include step (a) in which the electrodes 64 come into contact with an inner wall of a heart, step (b) in which locations of FBGs are calculated, step (c) in which locations of the electrodes 64 are calculated, and step (d) in which a 3D shape of the heart is constructed.

In the step (a), a physiological response may be measured from an electrode exposed on a surface of a mapping catheter including an optical fiber having a plurality of FBGs.

In the step (b), coordinates of the FBGs located on a same cross section as the electrode from which the response is measured in the step (a) may be calculated.

In the step (c), a coordinate of the electrode from which the physiological response is measured may be calculated from the coordinates of the FBGs calculated in the step (b).

In the step (d), the 3D shape of the heart may be constructed by sampling the coordinate of the electrode calculated in the step (c).

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A three-dimensional (3D) heart mapping system, comprising:

a mapping catheter including at least three optical cores each having a plurality of fiber Bragg gratings (FBGs) disposed in a lengthwise direction of a catheter body, wherein the spacing between the adjacent fiber Bragg gratings of the plurality of fiber Bragg gratings arranged along the catheter body increases in a distal direction of the catheter body, and a plurality of electrodes disposed in the lengthwise direction of the catheter body and exposed on an outer circumferential surface of the catheter body, wherein the plurality of electrodes are configured to come into contact with an inner wall of a heart; and a mapping processor configured to calculate coordinates of the plurality of FBGs based on optical wavelength information of reflected light received from the at least three optical cores and calculate coordinates of the plurality of electrodes from the coordinates of the plurality of FBGs and construct a 3D shape of the heart by using sample points of the plurality of electrodes configured to be in contact with the inner wall of the heart.

2. The 3D heart mapping system of claim 1, wherein the mapping catheter includes the catheter body having a first area defined by a path formed with at least one channel, and a second area defined by a front end provided with a tip to be condensed as an external force is applied, and the plurality of FBGs are configured to sense the 3D shape of the catheter body based on optical wavelength information of a group of the plurality of FBGs disposed in the first area, and sense the external force applied to the tip based on optical wavelength information of another group of the plurality of FBGs disposed in the second area.

3. The 3D heart mapping system of claim 1, wherein the mapping catheter is configured to form a loop at a front end, when the plurality of electrodes are connected to respective driving wires and the catheter body is bent at points at which the plurality of electrodes are located by the driving wires being pulled in or pulled out, and the mapping processor is configured to calculate coordinates of plurality of FBGs corresponding to locations of the plurality of electrodes at which a pressure is sensed when the loop is configured to come into contact with the inner wall of the heart, and to obtain the sample points in a linear form.

4. The 3D heart mapping system of claim 3, wherein the mapping catheter is configured to be steered to scan the inner wall of the heart by the loop.

5. The 3D heart mapping system of claim 1, wherein the mapping processor includes:

a control module configured to set a path of the mapping catheter to remotely control the mapping catheter, wherein the control module is configured to measure a pressure to be applied to a tip of the mapping catheter using optical wavelength information by the plurality of FBGs, and set a branch point entering the heart based on a pattern of change in external force generated when the tip is not in contact with blood vessels.

6. A three-dimensional (3D) heart mapping method, comprising:

step (a) of measuring a physiological response from an electrode exposed on a surface of a mapping catheter, wherein the mapping catheter includes an optical fiber having a plurality of fiber Bragg gratings (FBGs) disposed in a lengthwise direction of a catheter body, wherein the spacing between the adjacent fiber Bragg gratings of the plurality of fiber Bragg gratings arranged along the catheter body increases in a distal direction of the catheter body;

step (b) of calculating coordinates of the plurality of FBGs located on a same cross section as the electrode from which the physiological response is measured in step (a);

step (c) of calculating a coordinate of the electrode from which the physiological response is measured, from the coordinates of the plurality of FBGs calculated in step (b); and step (d) of constructing a 3D shape of a heart by sampling the coordinate of the electrode calculated in step (c).

7. A mapping catheter comprising:

a catheter body having a first area defined by a path in which at least one channel is formed, and a second area defined by a front end at which a tip to be condensed as an external force is applied is provided;

an optical fiber penetrating in the at least one channel and having a plurality of fiber Bragg gratings (FBG)s disposed in a lengthwise direction of the catheter body, wherein the spacing between the adjacent fiber Bragg gratings of the plurality of fiber Bragg gratings arranged along the catheter body increases in a distal direction of the catheter body; and a plurality of electrodes exposed on a surface of the catheter body and disposed in the lengthwise direction of the catheter body, wherein the FBGs are configured to sense a shape of the catheter body on which the electrodes are located based on optical wavelength information associated with optical wavelengths that change when the catheter body is configured to come into contact with an inner wall of a heart.

* * * * *